United States Patent
Shah et al.

(10) Patent No.: US 8,850,688 B2
(45) Date of Patent: Oct. 7, 2014

(54) METHOD OF MAKING A SENSOR WITH LAYERED ELECTRODES

(75) Inventors: Rajiv Shah, Rancho Palos Verdes, CA (US); Rebecca K. Gottlieb, Culver City, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 900 days.

(21) Appl. No.: 12/980,255

(22) Filed: Dec. 28, 2010

(65) Prior Publication Data

US 2011/0097480 A1 Apr. 28, 2011

Related U.S. Application Data

(60) Continuation of application No. 12/229,206, filed on Aug. 20, 2008, now Pat. No. 7,882,611, which is a division of application No. 11/234,523, filed on Sep. 23, 2005, now Pat. No. 7,725,148.

(51) Int. Cl.
| | |
|---|---|
| *H01S 4/00* | (2006.01) |
| *A61B 5/1486* | (2006.01) |
| *A61B 5/145* | (2006.01) |
| *A61B 5/00* | (2006.01) |
| *C12Q 1/00* | (2006.01) |

(52) U.S. Cl.
CPC ......... *A61B 5/14865* (2013.01); *A61B 5/14532* (2013.01); *A61B 5/6848* (2013.01); *A61B 5/6849* (2013.01); *C12Q 1/006* (2013.01)
USPC ..... 29/592.1; 29/825; 204/403.01; 205/777.5

(58) Field of Classification Search
CPC ........... A61B 5/14532; A61B 5/14865; A61B 5/6948; A61B 5/6849; C12Q 1/006
USPC ........... 29/592.1, 825; 204/403.01; 205/777.5
See application file for complete search history.

(56) References Cited

U.S. PATENT DOCUMENTS

| | | | |
|---|---|---|---|
| 4,218,298 | A | 8/1980 | Shimada et al. |
| 4,433,072 | A | 2/1984 | Pusineri et al. |

(Continued)

FOREIGN PATENT DOCUMENTS

| | | |
|---|---|---|
| EP | 1338295 A1 | 8/2003 |
| WO | WO 96/37246 A1 | 11/1996 |

(Continued)

OTHER PUBLICATIONS

Reach et al., "Experience with an implantable glucose sensor as a prerequisite of an artificial beta cell," Biomed. Biochim. Acta, 1984, pp. 577-584, vol. 5.

(Continued)

*Primary Examiner* — Carl Arbes
(74) *Attorney, Agent, or Firm* — Pillsbury Winthrop Shaw Pittman LLP

(57) ABSTRACT

A thin film sensor, such as a glucose sensor, is provided for transcutaneous placement at a selected site within the body of a patient. The sensor includes several sensor layers that include conductive layers and includes a proximal segment defining conductive contacts adapted for electrical connection to a suitable monitor, and a distal segment with sensor electrodes for transcutaneous placement. The sensor electrode layers are disposed generally above each other, for example with the reference electrode above the working electrode and the working electrode above the counter electrode. The electrode layers are separated by dielectric layer.

27 Claims, 5 Drawing Sheets

(56) References Cited

U.S. PATENT DOCUMENTS

| | | |
|---|---|---|
| 4,494,950 A | 1/1985 | Fischell |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,726 A | 3/1988 | Allen, III |
| 4,781,798 A | 11/1988 | Gough |
| 4,871,351 A | 10/1989 | Feingold |
| 5,080,653 A | 1/1992 | Voss et al. |
| 5,097,122 A | 3/1992 | Colman et al. |
| 5,101,814 A | 4/1992 | Palti |
| 5,108,819 A | 4/1992 | Heller et al. |
| 5,165,407 A | 11/1992 | Wilson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,320,725 A | 6/1994 | Gregg et al. |
| 5,322,063 A | 6/1994 | Allen et al. |
| 5,356,786 A | 10/1994 | Heller et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,437,999 A | 8/1995 | Diebold et al. |
| 5,482,473 A | 1/1996 | Lord et al. |
| 5,492,611 A | 2/1996 | Sugama et al. |
| 5,497,772 A | 3/1996 | Schulman et al. |
| 5,543,326 A | 8/1996 | Heller et al. |
| 5,569,186 A | 10/1996 | Lord et al. |
| 5,586,553 A | 12/1996 | Halili et al. |
| 5,593,852 A | 1/1997 | Heller et al. |
| 5,660,163 A | 8/1997 | Schulman et al. |
| 5,665,065 A | 9/1997 | Colman et al. |
| 5,665,222 A | 9/1997 | Heller et al. |
| 5,696,314 A | 12/1997 | McCaffrey et al. |
| 5,750,926 A | 5/1998 | Schulman et al. |
| 5,779,665 A | 7/1998 | Mastrototaro et al. |
| 5,791,344 A | 8/1998 | Schulman et al. |
| 5,798,031 A | 8/1998 | Charlton et al. |
| 5,904,708 A | 5/1999 | Goedeke |
| 5,917,346 A | 6/1999 | Gord et al. |
| 5,965,380 A | 10/1999 | Heller et al. |
| 5,972,199 A | 10/1999 | Heller et al. |
| 5,999,848 A | 12/1999 | Gord et al. |
| 5,999,849 A | 12/1999 | Gord et al. |
| 6,004,441 A | 12/1999 | Fujiwara et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,259,937 B1 | 7/2001 | Schulman et al. |
| 6,284,478 B1 | 9/2001 | Heller et al. |
| 6,309,526 B1 | 10/2001 | Fujiwara et al. |
| 6,329,161 B1 | 12/2001 | Heller et al. |
| 6,413,393 B1 | 7/2002 | Van Antwerp et al. |
| 6,418,332 B1 | 7/2002 | Mastrototaro et al. |
| 6,472,122 B1 | 10/2002 | Schulman et al. |
| 6,484,045 B1* | 11/2002 | Holker et al. ............ 600/345 |
| 6,484,046 B1 | 11/2002 | Say et al. |
| 6,503,381 B1 | 1/2003 | Gotoh et al. |
| 6,514,718 B2 | 2/2003 | Heller et al. |
| 6,551,496 B1 | 4/2003 | Moles et al. |
| 6,554,798 B1 | 4/2003 | Mann et al. |
| 6,558,320 B1 | 5/2003 | Causey, III et al. |
| 6,560,471 B1 | 5/2003 | Heller et al. |
| 6,565,509 B1 | 5/2003 | Plante et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,793,802 B2 | 9/2004 | Lee et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,118,667 B2 | 10/2006 | Lee |
| RE39,390 E | 11/2006 | Hasegawa et al. |
| 7,138,041 B2 | 11/2006 | Su et al. |
| 7,276,029 B2 | 10/2007 | Goode, Jr. et al. |
| 7,310,544 B2 | 12/2007 | Brister et al. |
| 7,467,003 B2 | 12/2008 | Brister et al. |
| 7,494,465 B2 | 2/2009 | Brister et al. |
| 7,497,827 B2 | 3/2009 | Brister et al. |
| 2002/0029964 A1 | 3/2002 | Matsumoto |
| 2002/0082665 A1 | 6/2002 | Haller et al. |
| 2002/0161288 A1 | 10/2002 | Shin et al. |
| 2003/0077642 A1 | 4/2003 | Fritsch et al. |
| 2003/0078560 A1 | 4/2003 | Miller et al. |
| 2003/0088166 A1 | 5/2003 | Say et al. |
| 2003/0152823 A1 | 8/2003 | Heller et al. |
| 2003/0168338 A1 | 9/2003 | Gao et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0067166 A1 | 4/2004 | Karinka et al. |
| 2004/0074785 A1* | 4/2004 | Holker et al. ............ 205/777.5 |
| 2004/0093167 A1 | 5/2004 | Braig et al. |
| 2004/0111017 A1 | 6/2004 | Say et al. |
| 2005/0124020 A1 | 6/2005 | Lee et al. |
| 2005/0143635 A1 | 6/2005 | Kamath et al. |
| 2005/0164322 A1 | 7/2005 | Heller et al. |
| 2005/0177035 A1 | 8/2005 | Botvinick et al. |
| 2005/0214585 A1 | 9/2005 | Li et al. |
| 2007/0173711 A1 | 7/2007 | Shah et al. |
| 2007/0227907 A1 | 10/2007 | Shah et al. |
| 2008/0135408 A1 | 6/2008 | Sjolander |
| 2008/0313896 A1 | 12/2008 | Shah et al. |

FOREIGN PATENT DOCUMENTS

| | | | |
|---|---|---|---|
| WO | | 0158348 A2 * | 8/2001 |
| WO | WO | 01/58348 A2 | 8/2001 |
| WO | WO | 01/58348 A3 | 8/2001 |
| WO | WO | 02/058537 A2 | 8/2002 |

(56) References Cited

OTHER PUBLICATIONS

Abel et al., "A Method for Evaluating in vivo the Functional Characteristics of Glucose Sensors," Biosensors, 1986, pp. 211-220, vol. 2.
Boguslavsky et al., "Applications of redox polymers in biosensors," Solid State Ionics, 1993, pp. 189-197, vol. 60.
Geise et al., "Electropolymerized 1,3-diaminobenzene for the construction of a 1-1'-dimethylferrocene mediated glucose biosensor,"Analytica Chim. Acta.,1993, pp. 467-473, v18.
Gernet et al., "A planar glucose enzyme electrode," Sensors and Actuators, 1989, pp. 537-540, vol. 17, Elsevier Sequoia, Netherlands.
Gernet et al., "Fabrication and Characterization of a Planar Electrochemical Cell and its Applications as a Glucose Sensor," Sensors and Actuators, 1989, pp. 49-70, vol. 18.
Gorton et al., "Amperometric glucose senosrs based on immobilized glucose-oxidizing enzymes and chemically modified electrodes," Analytica Chim Acta., 1991, pp. 43-54, v. 249.
Gorton et al., "Amperometric biosensors based on an apparent direct electron transfer between electrodes and immobilized peroxidases," Analyst, 1992, pp. 1235-1241, vol. 117.
Gough et al., "Two-Dimensional Enzyme Electrode Sensor for Glucose," Analytical Chemistry, 1985, pp. 2351-2357, vol. 57.
Gregg et al., "Redox polymer films containing enzymes," J. Phys. Chem., 1991, pp. 5970-5975.
Gregg et al., "Cross-Linked Redox Gels Containing Glucose Oxidase for Amperometric Biosensor Applications," Anal. Chem., 1990, pp. 258-263, vol. 62.
Heller et al., "Electrical Wiring of Redox Enzymes," Accounts of Chemical Research, 1990, pp. 128-134, vol. 23, No. 5.
Johnson et al., "In vivo evaluation of an electroenzymatic glucose sensor implanted in subcutaneous tissue," Biosensors & Bioelectronics, 1992, pp. 709-714, vol. 7.
Jonsson et al., "An Electrochemical Sensor for Hydrogen Peroxide Based on Peroxidase Adsorbed on a Spectrographic Graphite Electrode," Electroanalysts, 1989, pp. 465-468, v. 1.
Kanapieniene et al., "Miniature glucose biosensor with extended linearity," Sensors and Actuators, 1992, pp. 37-40, vol. B, No. 10.
Kawamori et al., "Perfect Normalization of Excessive Glucagon Responses to Intravenous Arginine in Human Diabetes Mellitus With . . . ," Diabetes, 1980, pp. 762-765, vol. 29.
Kimura et al., "An immobilized Enzyme Membrane Fabrication Method using an Ink Jet Nozzle," Biosensors, 1988, pp. 41-52, vol. 4.
Koudelka et al., "In-vivio Behaviour of Hypodermically Implanted Microfabricated Glucose Sensors," Biosensors & Bioelectronics, 1991, pp. 31-36, vol. 6.
Mastrototaro et al., "An electroenzymatic glucose sensor fabricated on a flexible substrate," Sensors and Actuators, 1991, pp. 139-144, vol. 5.
Mastrototaro et al., "An Electroenzymatic Sensor Capable of 72 Hour Continuous Monitoring of Subcutaneous Glucose," 14th Int'l Diabetes Federation Congress, 1991.
McKean et al., "A Telemetry-Instrumentation System for Chronically Implanted Glucose and Oxygen Sensors," IEEE Transactions on Biomedical Eng., 1988, pp. 526-532, vol. 35, No. 7.
Monroe, "Novel implantable glucose sensors," ACL, 1989, pp. 8-16.
Morff et al., "Microfabrication of Reproducible, Economical, Electroenzymatic Glucose Sensors," Annual Int'l Conf. IEEE Eng. in Med. and Bio. Soc., 1990, pp. 483-484, v.12, n. 2.
Nakamato et al., "A Lift-Off Method for Patterning Enzyme-Immobilized Membranes in Multi-Biosensors," Sensors and Actuators, 1988, pp. 165-172, vol. 13.
Nishida et al., "Clinical applications of the wearable artificial endocrine pancreas with the newly designed . . . ," Path. and Treat. of NIDDM . . . , 1994, p. 353-358, No. 1057.
Shichiri et al., "An artificial endocrine pancrease—problems awaiting solutions for long term clinical applications of . . . ," Frontiers Med. Biol. Eng., 1991, pp. 283-292, v.3.
Shichiri et al., "Wearable Artificial Endocrine Pancreas with Needle-Type Glucose Sensor," The Lancet, 1982, pp. 1129-1131, vol. 2 (8308).
Shichiri et al., "Telemetry Glucose Monitoring Device with Needle-Type Glucose Sensor," Diabetes Care, May-Jun. 1986, pp. 298-301, vol. 9, No. 3.
Shichiri et al., "Normalization of the Paradoxic Secretion of Glucagen in Diabetics Who Were Controlled by the Artificial Beta Cell," Diabetes, 1979, pp. 272-275, vol. 28.
Shichiri et al., "Closed-Loop Glycemic Control with a Wearable Artificial Endocrine Pancreas," Diabetes, 1984, pp. 1200-1202, vol. 33.
Shichiri et al., "In Vivo Characteristics of Needle-Type Glucose Sensor," Hormone and Metabolic Research, 1988, pp. 17-20, vol. 20.
Shichiri et al., "A Needle-Type Glucose Sensor," Life Support Systems: The Journal of the European Society for Artificial Organs, 1984, pp. 7-9, vol. 2, supplement 1.
Shichiri et al., "The Wearable Artificial Endocrine Pancreas with a Needle-Type Glucose Sensor," Acta Pediatr, Jpn, 1984, pp. 358-370, vol. 26.
Shichiri et al., "Glycaemic Control in Pancreatectomized Dogs with a Wearable Artificial Endocrine Pancreas," Diabetologica, 1983, pp. 179-184, vol. 24.
Shichiri et al., "Membrane design for extending the long-life of an implantable glucose sensor," Diab. Nutr. Metab., 1989, pp. 309-313, vol. 2.
Shinkai et al., "Molecular Recognition of Mono- and Di-Saccharides by Phenylboronic Acids in Solvent Extraction and as a Monolayer," J. Chem. Soc., 1991, pp. 1039-1041.
Tamiya et al., "Micro Glucose Sensors Using Electron Mediators Immobilized on a Polypyrrole-Modified Electrode," Sensors and Actuators, 1989, pp. 297-307, v.18.
Tsukagoshi et al., "Specific Complexation with Mono- and Disaccharides That Can Be Detected by Circular Dichroism," J. Org. Chem., 1991, pp. 4089-4091, vol. 56.
Urban et al., "Minaturized multi-enzyme biosensors integrated with pH sensors on flexible polymer carriers . . . ," Biosensors & Bioelectronics, 1992, pp. 733-739, vol. 7.
Urban et al., "Miniaturized thin-film biosensors using covalently immobilized glucose oxidase," Biosensors & Bioelectronics, 1991, pp. 555-562, vol. 6.
Velho et al., "In vivo calibration of a subcutaneous glucose sensor for determination of subcutaneous glucose kinetics," Diab. Nutr. Metab., 1988 pp. 227-233, v.3.
Yokoyama et al., "Integrated Biosensor for Glucose and Galactose," Analytica Chimica Acta., 1989, pp. 137-142, vol. 218.
Nishida et al., "Development of a ferrocene-mediated needle-type glucose sensor . . . ," Medical Process Through Technology, 1995, pp. 91-103, vol. 21.
Koudelka et al., "Planar Amperometric Enzyme-Based Glucose Microelectrode," Sensors and Actuators, 1989, pp. 157-165, vol. 18.
Yamasaki et al., "Direct measurement of whole blood glucose by a needle-type sensor," Clinica Chimica Acta., 1989, pp. 93-98, vol. 93.
Sternberg et al., "Study and Development of Multilayer Needle-type Enzyme-based Glucose Microsensors," Biosensors, 1988, pp. 27-40, vol. 4.
Shaw et al., "In vitro testing of a simply constructed, highly stable glucose sensor suitable for implantation . . . ," Biosensors & Bioelectronics, 1991, pp. 401-406, vol. 6.
Poitout et al., "A glucose monitoring system for on line estimation in man of blood glucose concentration using a miniaturized . . . ," Diabetologia, 1993, pp. 658-663, vol. 36.
Hashigushi et al., "Development of a Miniaturized Glucose Monitoring System by Combining a Needle-Type Glucose Sensor . . . ," Diabetes Care, 1994, pp. 387-389, v.17, n. 5.
Jobst et al., "Thin-Film Microbiosensors for Glucose-Lactate Monitoring," Anal. Chem., 1996, p. 3173-79, vol. 68.
Shults et al., "A Telemetry-Instrumentation System for Monitoring Multiple Subcutaneously Implanted Glucose Sensors," IEEE Trans. on Biomed. Eng., 1994, pp. 937-942, v41, n. 10.
Wang et al., "Needle-Type Dual Microsensor for the Simultaneous Monitoring of Glucose and Insulin," Anal. Chem., 2001, pp. 844-847, vol. 73.

(56) References Cited

OTHER PUBLICATIONS

Moussey et al., "Performance of Subcutaneously Implanted Needle-Type Glucose Sensors Employing a Novel Trilayer Coating," Anal. Chem., 1993, 2072-77, vol. 65.

Bindra et al., "Design and In Vitro Studies of a Needle-Type Glucose Sensor for Subcutaneous Monitoring," Anal. Chem., 1991, pp. 1692-1696, vol. 63.

PCT International Search Report, Feb. 26, 2007 (PCT/US2006/035382) (4-pgs).

* cited by examiner

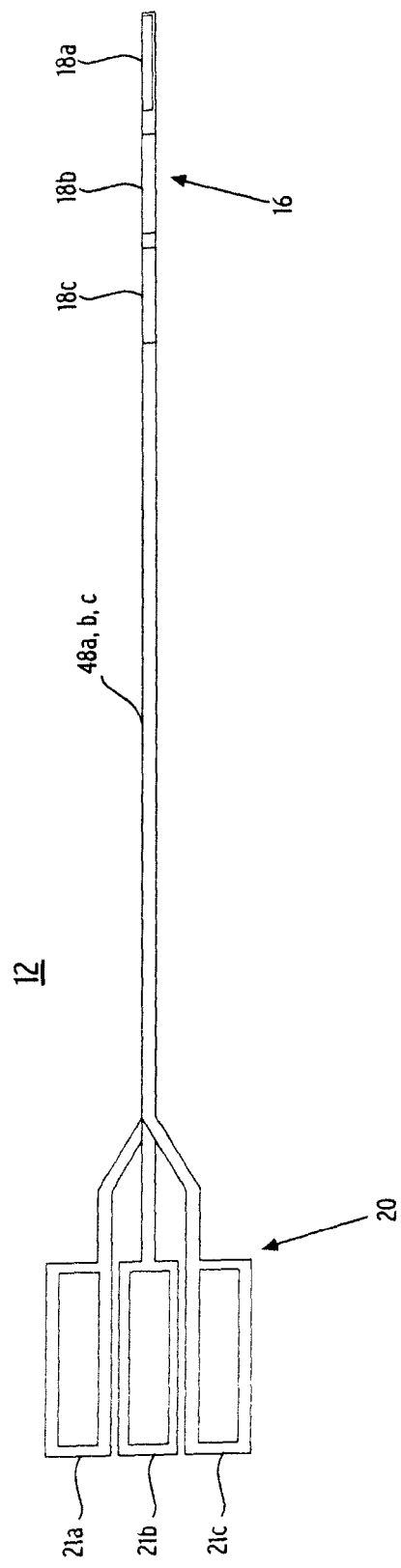
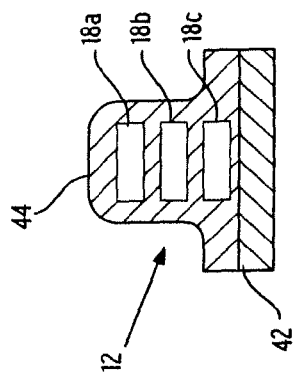

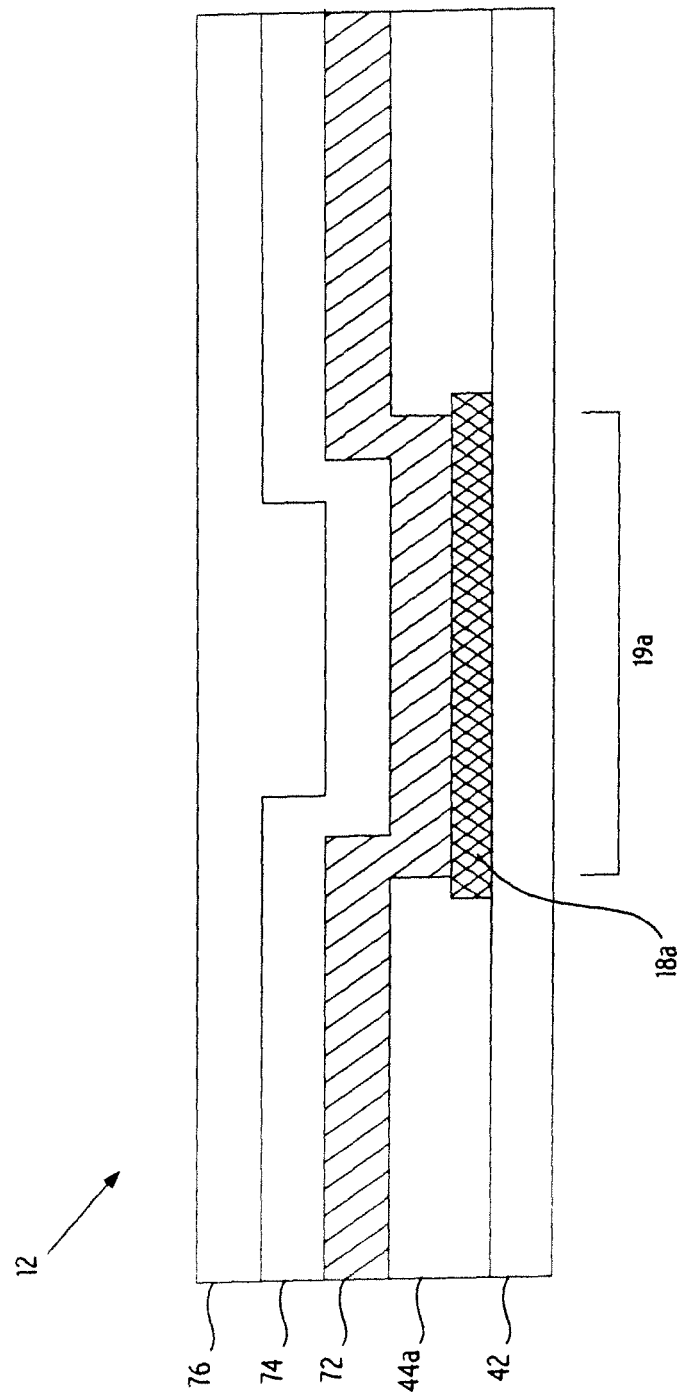

METHOD OF MAKING A SENSOR WITH LAYERED ELECTRODES

RELATED APPLICATION DATA

This is a continuation of U.S. patent application Ser. No. 12/229,206, filed Aug. 20, 2008, now U.S. Pat. No. 7,882,611, which is a divisional of U.S. patent application Ser. No. 11/234,523, filed Sep. 23, 2005, now U.S. Pat. No. 7,725,148, all of which are incorporated herein by reference.

BACKGROUND OF THE INVENTION

1. Field of the Invention

This invention relates generally to a sensor and methods for manufacturing a sensor for placement at a selected site within the body of a patient. More specifically, this invention relates to the positioning of electrodes in an improved flexible thin film sensor of the type used, for example, to obtain periodic blood glucose (BG) readings.

2. Description of Related Art

Thin film electrochemical sensors are generally known in the art for use in a variety of specialized sensor applications. Such thin film sensors generally comprise one or more thin conductors applied by photolithography mask and etch techniques between thin layers of a nonconductive film material, such as polyimide film. The conductors are shaped to define distal segment ends having an appropriate electrode material thereon, in combination with proximal end contact pads adapted for conductive connection with appropriate electronic monitoring equipment. In recent years, thin film sensors of this general type have been proposed for use as a transcutaneous sensor in medical applications. As one example, thin film sensors have been designed for use in obtaining an indication of BG levels and monitoring BG levels in a diabetic patient, with the distal segment portion of the electrodes positioned subcutaneously in direct contact with patient blood. Such readings can be especially useful in adjusting a treatment regimen which typically includes regular administration of insulin to the patient. In this regard, BG readings are particularly useful in conjunction with semiautomated medication infusion pumps of the external type, as generally described in U.S. Pat. Nos. 4,562,751; 4,678,408; and 4,685,903; or automated implantable medication infusion pumps, as generally described in U.S. Pat. No. 4,573,994.

Relatively small and flexible electrochemical sensors have been developed for subcutaneous placement of sensor electrodes in direct contact with patient blood or other extracellular fluid, wherein such sensors can be used to obtain periodic readings over an extended period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal segment for transcutaneous placement in direct contact with patient blood or the like, and exposed conductive contacts at an externally located proximal segment end for convenient electrical connection with a suitable monitor device. Such thin film sensors hold significant promise in patient monitoring applications, but unfortunately have been difficult to place transcutaneously with the sensor electrodes in direct contact with patient blood or other extracellular fluid. Improved thin film sensors and related insertion sets are described in commonly assigned U.S. Pat. Nos. 5,299,571, 5,390,671; 5,391,250; 5,482,473; 5,568,806; and 5,586,553 and International Publication No. WO 2004/036183, which are incorporated by reference herein.

BRIEF SUMMARY OF THE INVENTION

The present invention relates specifically to an improved sensor adapted to have a thin configuration for quick and easy placement of the film sensor on a patient with sensor electrodes in direct contact with patient blood or other extracellular fluid.

In accordance with embodiments of the invention, a sensor, such as a flexible thin film electrochemical sensor, is provided that may be placed at a selected site within the body of the patient. In certain embodiments, the sensor includes several electrodes, configured so that the overall size of the sensor is thinner than traditional sensors. In an embodiment of the present invention, the sensor includes electrodes in electrode layers positioned generally above each other. The electrodes and traces from the electrodes to contact pads, which are adapted to connect to sensor electronics, may be horizontally displaced from each other with other materials layered in between. The electrodes themselves may be in a staggered configuration so that the lower electrodes extend further, allowing portions of the electrodes to be exposed. Each of the electrodes may also be of the same size or different sizes. In the layered configuration, the electrode layers are staggered to expose a part of each electrode to contact the patient fluid.

In further embodiments of the invention, the electrodes may include a working electrode and a counter electrode and may further include a reference electrode. Alternatively, the electrodes may include more or fewer electrodes, depending on the desired use. The electrodes may comprise gold and chrome and/or other adhesive/conductive layers, such as titanium, platinum, tungsten, etc. The working and counter electrodes may be plated with platinum black and the reference electrode may be plated with silver and silver chloride. For glucose sensing, the sensor may include a layer of glucose oxidase, which may be mixed with albumin. Over the glucose oxidase may be a glucose limiting membrane, such as one that includes a polyamine, such as polyoxypropylene-diamine sold under the trademark JEFFAMINE®, and polydimethylsiloxane. There may be a hydrophilic membrane over the glucose limiting membrane.

In an embodiment of the invention, a subcutaneous insertion set is provided for placing the sensor at a selected site within the body of a patient. The insertion set comprises the sensor and further comprises a slotted insertion needle extending through a mounting base adapted for seated mounting onto the patient's skin. The flexible thin film sensor includes a proximal segment carried by the mounting base, and a distal segment protruding from the mounting base and having one or more sensor electrodes thereon. The distal segment of the sensor is carried within a protective cannula which extends from the mounting base with a portion of the cannula being slidably received within the insertion needle. One or more apertures foimed in the cannula are positioned in general alignment with the staggered sensor electrodes on the sensor distal segment.

In embodiments of the invention, when the mounting base is pressed onto the patient's skin, the insertion needle pierces the skin to transcutaneously place the cannula with the sensor distal segment therein. The insertion needle can be withdrawn from the mounting base, leaving the cannula and sensor distal segment within the patient, with the sensors electrodes thereon exposed through the aperture or apertures for direct contact with to patient fluid at the selected position within the patient, such as a subcutaneous, intravascular, intramuscular, or intravenous site. Other sites may include intraorgan and interperitoneal sites. Conductive contacts on the sensor proximal segment end can be electrically connected to a suitable monitor device so that appropriate blood chemistry readings can be taken.

In further embodiments of the invention, during insertion, the insertion needle and the protective cannula cooperatively protect and guide the sensor to the desired transcutaneous placement position. The insertion needle can then be withdrawn, whereupon the slotted needle geometry permits the insertion needle to slide over and longitudinally separate from the second portion of the cannula, thereby leaving the cannula and sensor therein at the selected insertion site.

Other features and advantages of the present invention will become more apparent from the following detailed description, taken in conjunction with the accompanying drawings which illustrate, by way of example, the principles of the invention.

BRIEF DESCRIPTION OF THE DRAWINGS

A detailed description of embodiments of the invention will be made with reference to the accompanying drawings, wherein like numerals designate corresponding parts in the figures.

FIG. 2 is an enlarged side view of a sensor according to an embodiment of the invention;

FIG. 3 is an enlarged cross-sectional view taken generally on the line 2-2 of FIG. 1c;

FIG. 4 is an enlarged cross-sectional view taken generally on the line 3-3 of FIG. 1c;

DETAILED DESCRIPTION

Figure 1A:
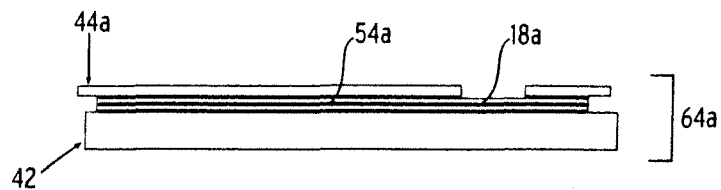
FIG. 1a is an enlarged fragmented sectional view of a sensor according to an embodiment of the invention.

In the following description, reference is made to the accompanying drawings which form a part hereof and which illustrate several embodiments of the present inventions. It is understood that other embodiments may be utilized and structural and operational changes may be made without departing from the scope of the present inventions.

In embodiments of the present invention, a method is provided for producing electrochemical sensors of the type used, for example, in subcutaneous or transcutaneous monitoring of analytes in a patient. For example, they may be used for monitoring of blood glucose levels in a diabetic patient. The sensors of the invention may also be used for sensing other analytes, such as lactate. While certain embodiments of the invention pertain to glucose sensors, the structure of the sensor disclosed and methods of creating the sensor can be adapted for use with any one of the wide variety of sensors known in the art. A number of enzyme sensors (e.g., glucose sensors that use the enzyme glucose oxidase to effect a reaction of glucose and oxygen) are known in the art. See, for example, U.S. Pat. Nos. 5,165,407, 4,890,620, 5,390,671 and 5,391,250, and International Publication No. WO 2004/036183, which are herein incorporated by reference. Sensors for monitoring glucose concentration of diabetics are further described in Schichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al., "In Vivo Measurement of Subcutaneous Glucose Concentrations with an Enzymatic Glucose Sensor and a Wick Method," Klin. Wochenschr. 67:491-495 (1989); and Pickup, et al., "In Vivo Molecular Sensing in Diabetes Mellitus: An Implantable Glucose Sensor with direct Electron Transfer," Diabetologia 32:213-217 (1989), which are herein incorporated by reference. Other sensors are described, for example, in Reach, et al., ADVANCES IN IMPLANTABLE DEVICES, A. Turner (ed.), JAI Press, London, Chap. 1, (1993), which is herein incorporated by reference.

The electrochemical sensors of embodiments of the invention are film sensors that include several electrodes, configured so that the overall size of the sensor is thinner than traditional sensors. In further embodiments of the present invention, the sensor includes three electrodes that are each positioned generally above the other, although the term "above" is intended to mean generally disposed in a plane vertically on top of each other, not necessarily directly over or disposed on one another. For example, the electrodes may be above and adjacent to another electrode, such as offset horizontally. The sensor of the invention may have only two electrodes or more than three electrodes. In an embodiment with three electrodes, each of the three electrodes may be of the same size or different sizes. In particular embodiments, the electrode layers are staggered to expose at least a portion of each electrode to contact the patient fluid. The three sensor electrodes may all serve different functions. For example, there may be a working electrode, a counter electrode, and a reference electrode. The reference electrode facilitates the filtering out of background chemical reactions that could detract from a correct reading of the BG level. In between layers of the sensor electrodes, a layer of insulation or dielectric material may be spread so that there is no communication between the individual electrodes.

The exposed portions of the electrodes are coated with a thin layer of material having an appropriate chemistry. For example, an enzyme such as glucose oxidase, glucose dehydrogenase, or hexokinase can be disposed on the exposed portion of the sensor element within an opening or aperture defined in a cover layer.

Figure 1B:
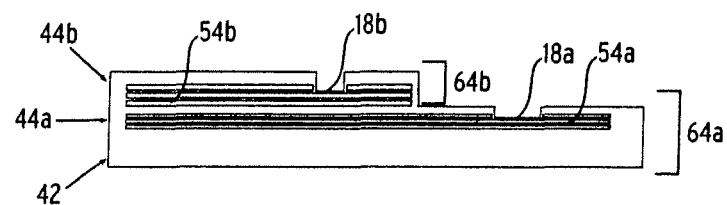
FIG. 1b is an enlarged fragmented sectional view corresponding generally with a first and second electrode layer of a sensor according to an embodiment of the invention.
Figure 1C:
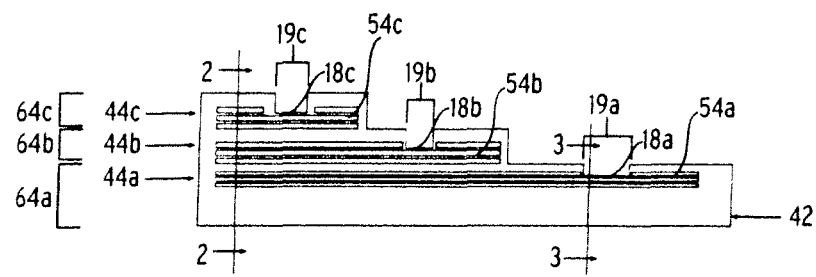
FIG. 1c is an enlarged fragmented sectional view corresponding generally with a first, second, and third electrode layer of a sensor according to an embodiment of the invention.

FIGS. 1a-c illustrate longitudinal cross-sections of an embodiment of the invention where the various layers of the distal end 16 of the sensor 12 (shown in FIG. 2), specifically the sensor layers 64a, 64b, and 64c, are shown. In the illustrated embodiment, there are three metallization steps taken to form the electrodes 18a, 18b, and 18c. The metallization process forms one or more conductive layers/electrode layers 54a, 54b, and 54c on top of a base layer 42. The base layer 42 is generally an electrically insulating layer such as a polyimide substrate, which may be self-supporting or further supported by another material. In one embodiment, the base layer 42 comprises a polyimide tape, dispensed from a reel. Providing the base layer 42 in this form can facilitate clean, high density mass production. Further, in some production processes using such a polyimide tape, sensors can be produced on both sides of a tape.

FIG. 2 illustrates an enlarged fragmented sectional view of a sensor according to an embodiment of the invention. The electrodes 18a, 18b, and 18c at the distal end 16 of the sensor 12 lead through traces 48a, 48b, and 48c to conductive pads 21a, 21b, and 21c at a proximal end 20 of the sensor. Although the figures and the description below describes the formation and structure of a sensor with three electrodes, the method and structure can be used in a sensor of fewer or more electrodes.

The first metallization step, shown in FIG. 1a, applies the conductive layer 54a onto the insulative base layer 42. The conductive layer may be provided as a plurality of thin film conductive layers, such as an initial chrome-based layer suitable for chemical adhesion to the base layer, followed by subsequent formation of a thin film gold-based layer. Optionally, a chrome-based top layers may be formed on top of the thin film gold-based layer. The conductive layer may also be formed of gold and/or chrome in different ratios and/or other adhesive/conductive layers, such as titanium, platinum, tungsten, etc. In alternative embodiments, other electrode layer conformations or materials can be used. The conductive layer 54a can be applied using electrode deposition, surface sputtering or another suitable process step. The electrical circuit of each conductive layer typically comprises one or more conductive paths with regions at a proximal end to form contact pads and regions at a distal end to form sensor electrodes. Generally, etching is performed to define the electrical circuit of each layer. Alternatively, "lift off" may be used, in which the photoresist defines a pattern prior to metal sputtering, after which the photoresist is dissolved away (along with the unwanted metal), and the metal pattern is left behind. In further embodiments, photoresisting is performed to protect the metallized trace and electrode and photoimaging is performed to cure specified areas. For example, the conductive layer is covered with a selected photoresist coating, followed by an etch step resulting in one or more conductive paths. An electrically insulative cover layer (or dielectric layer) 44a, such as a polymer coating, is then applied over at least portions of the conductive layer 54a. Acceptable polymer coatings for use as the insulative cover layer 44a include, for example, non-toxic biocompatible polymers such as polyimide, biocompatible solder masks, epoxy acrylate copolymers, and the like. Further, these coatings can be photoimageable to facilitate photolithographic forming of apertures through to the conductive layer 54a to expose the electrode 18a. This first metallization step is finished by developing and rinsing the produced electrode 18a. In an embodiment this electrode 18a is the counter electrode. Alternatively, the electrode 18a may be a working or reference electrode.

The second metallization step, shown in FIG. 1b, applies a second conductive layer 54b over the first insulative cover layer 44a and covering and repeats the process of covering the second conductive layer 54b with another insulative cover layer 44b. This produces another electrode 18b, positioned generally above the first electrode 18a. In an embodiment, electrode 18b is the working electrode. Alternatively, the electrode 18b may be a counter or working electrode. The third metallization step, shown in FIG. 1c, repeats all of the previous steps to form a third electrode 18c. In an embodiment, electrode 18c is the reference electrode. Alternatively, the electrode 18c may be a working or counter electrode. As shown in FIG. 1c, the electrodes are in a staggered configuration, so that at least a portion of each electrode may be exposed. The conductive layers 54a, 54b and 54c, may be directly above each other or horizontally displaced from each other (into and out of the page). The electrodes may further be configured in any way that allows the electrodes to contact fluid when inserted into a body of a patient.

The sensor 12 is thus shown with the subsequent conductive layers 54a, 54b, and 54c alternating with the insulative layers 44a, 44b, and 44c. In between every two conductive layers there is an insulative layer that serves to isolate each conductive layer so that there is no trace communication between the layers. Apertures 19a, 19b, and 19c are formed in the top insulative cover layer 44c. Although the electrodes 18a, 18b, and 18c are shown as lying on top of each other, it is also possible to have them generally above each other, but spaced sideways so that they are not directly on top of each other (e.g., horizontally displaced). This is also true for the traces that lead to conductive contacts, which electrically connect to the sensor electronics, at the opposite end of the sensor from the electrodes. The apertures can be made through photolithographic development, laser ablation, chemical milling, etching, or the like. The exposed electrodes and/or contact pads can also undergo secondary processing through the apertures, such as additional plating processing, to prepare the surfaces, and/or strengthen the conductive regions.

As shown in FIG. 4, typically, a sensor chemistry layer 72 is disposed on one or more of the exposed electrodes (e.g., 18a) of the conductive layers. In certain embodiments, the sensor chemistry layer 72 is an enzyme layer, for example, glucose oxidase. If the enzyme layer is glucose oxidase, it reacts with glucose to produce hydrogen peroxide, which modulates a current to the electrode which can be monitored to measure an amount of glucose present. The sensor chemistry layer 72 can be applied over portions of the sensor 12 or over the entire sensor, including the protective layer (e.g., 44a). The sensor chemistry layer 72 is generally disposed on at least portions of a working electrode. In further embodiments, the sensory chemistry layer may be disposed on at least portions of other electrodes, such as a counter electrode. For example, if the electrode 18a in FIG. 4 is the counter electrode, then the sensor chemistry layer 72 is disposed on at least portions of the electrode 18a. Example methods for generating the sensor chemistry layer include spin coating processes, dip and dry processes, low shear spraying processes, ink-jet printing processes, silk screen processes, casting process, and the like.

In certain embodiments, the sensor chemistry layer 72 comprises glucose oxidase and a carrier protein. The glucose oxidase and carrier protein may be in a substantially fixed ratio. In further embodiments, the glucose oxidase and the carrier protein are distributed in a substantially uniform manner throughout the disposed enzyme layer. Typically, the carrier protein comprises albumin, generally in an amount of about 2-10% by weight, preferably about 5% by weight. As used herein, "albumin" refers to those albumin proteins typically used by artisans to stabilize polypeptide compositions, such as human serum albumin, bovine serum albumin, and the like. The application of the glucose oxidase and albumin mixture may be made, for example, by a spin coating process, a casting process, a screen printing process or a doctor blading process. Optionally, the glucose oxidase layer that is formed on the sensor is less than 2 microns in thickness. In further embodiments, the glucose oxidase layer may be less than 1, 0.5, 0.25 or 0.1 microns in thickness. The choice of the glucose oxidase layer thickness may be made to balance fast response and fast hydration verses a sensor lifetime. Generally, thin layers hydrate and respond more quickly, but do not last as long. Thick layers last a long time, but hydrate more slowly and respond to glucose more slowly.

The sensor chemistry layer 72 may be coated with one or more cover layers. In certain embodiments, as shown in FIG. 4, the cover layer 74 comprises a membrane that can regulate the amount of analyte that can contact the enzyme of the sensor chemistry layer 72. For example, the cover layer 74 can comprise a glucose limiting membrane, which regulates the amount of glucose that contacts the glucose oxidase enzyme layer on an electrode. Such glucose limiting membranes can be made from a wide variety of materials suitable for such purposes, such as, for example, silicone, polyurethane, cellulose acetate, Nafion, polyester sulfonic acid (Kodak AQ), hydrogels, etc. In further embodiments the glucose limiting membrane includes a polyamine, such as polyoxypropylene-diamine sold under the trademark JEFFAMINE®, and polydimethylsiloxane (Structure I) and/or a polysilane, such as polydimethylsiloxane (PDMS) (Structure II). In still further embodiments, the glucose limiting membrane is a random block copolymer made from JEFFAMINE® and PDMS. In further embodiments, the glucose limiting membrane may also, or alternatively, be a mechanically limiting membrane. For example, a glucose limiting membrane may be used that is an oxygen passing/glucose limiting polymer, such as silicone, and a small window with the correct ratio size may be cut into the polymer to meter glucose directly to the sensor surface.

STRUCTURE I

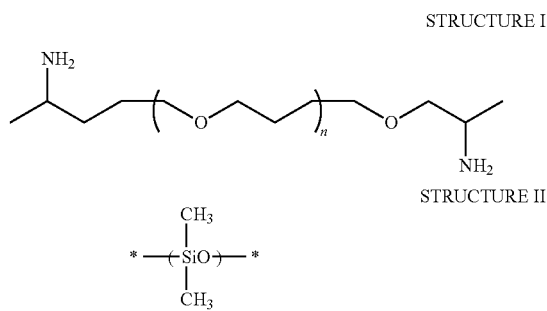

STRUCTURE II

In still further embodiments, the JEFFAMINE®, which is glucose permeable, and the PDMS, which is non-glucose permeable but oxygen permeable, are linked together with diisocyanide. By using this random block copolymer, an excess of oxygen by the glucose oxidase and the electrodes can be ensured along with a restricted amount of glucose.

In further embodiments, an adhesion promoter (not shown) is provided between the glucose limiting membrane 74 and the sensor chemistry layer 72 to facilitate contact and/or adhesion. The adhesion promoter layer can be made from any one of a wide variety of materials that facilitates bonding, for example materials comprising a silane compound, such as an aminopropyltriethoxy silane. Alternatively, protein or like molecules in the sensor chemistry layer 72 can be sufficiently crosslinked or otherwise prepared to allow the glucose limiting membrane 74 to be disposed in direct contact with the sensor chemistry layer in absence of an adhesion promoter layer. The adhesion promoter layer can be spin coated, sprayed, cast, etc. onto the enzyme layer. It may be exposed to heat and humidity to create silanol (sticky) groups. In further embodiments, the layer may be repeated. Although not necessary, the coating may help adhesion oxygen buffering. The time for exposure to heat and humidity is time sufficient to create silanol (sticky) groups, for example about two hours.

A hydrophilic membrane 76, which may be non-toxic and biocompatible, may be positioned above the glucose limiting membrane 74. The hydrophilic membrane 76 promotes tolerance of the sensor in the body.

Typically, the electrodes are formed by one of the variety of methods known in the art such as photoresist, etching and rinsing to define the geometry of the active electrodes. The electrodes can then be made electrochemically active, for example by electrodeposition of platinum black for the working and counter electrode, and silver followed by silver chloride on the reference electrode. The sensor chemistry layer is then disposed on the conductive layer by a method other than electrochemical deposition, usually followed by vapor crosslinking, for example with a dialdehyde, such as glutaraldehyde, or a carbodi-imide.

The electrodes and conductive layers are generally composed of conductive materials. However, they are not limited to conductive elements. Other useful sensor elements can be formed from any material that is capable of producing a detectable signal after interacting with a preselected analyte whose presence is to be detected. The detectable signal can be, for example, an optically detectable change, such as a color change or visible accumulation of the desired analyte (e.g., cells). Exemplary such materials include polymers that bind specific types of cells, single-strand DNA, antigens, antibodies and reactive fragments thereof, etc. Sensor elements can also be formed from materials that are essentially non-reactive (i.e., controls). The foregoing alternative sensor elements are beneficially included, for example, in sensors for use in cell-sorting assays and assays for the presence of pathogenic organisms, such as viruses (HIV, hepatitis-C, etc.), bacteria, protozoa, and the like.

As shown in FIGS. 2 and 3, in one embodiment of the present invention a sensor 12 has the three electrodes 18a, 18b, and 18c positioned generally one above the other. The three electrode layers comprise a plurality of elongated conductive traces 48a, 48b, and 48c connected to the electrodes 18a, 18b, and 18c on one end and connected to conductive pads 21a, 21b, and 21c on the opposing proximal segment 20. Each electrode layer is formed between an underlying insulative base layer 42 and an overlying insulative cover layer 44. Apertures (not shown) may be formed on the insulative cover layer 44 to expose the distal segment 16 and the proximal segment 20 of the electrodes. In a glucose monitoring application, the flexible sensor 12 is placed transcutaneously so that the distal segment 16 is in direct contact with patient blood or extracellular fluid, and wherein the proximal segment 20 is disposed externally for convenient connection, either by wired or wireless communication, to a monitoring device (not shown).

Figure 7:
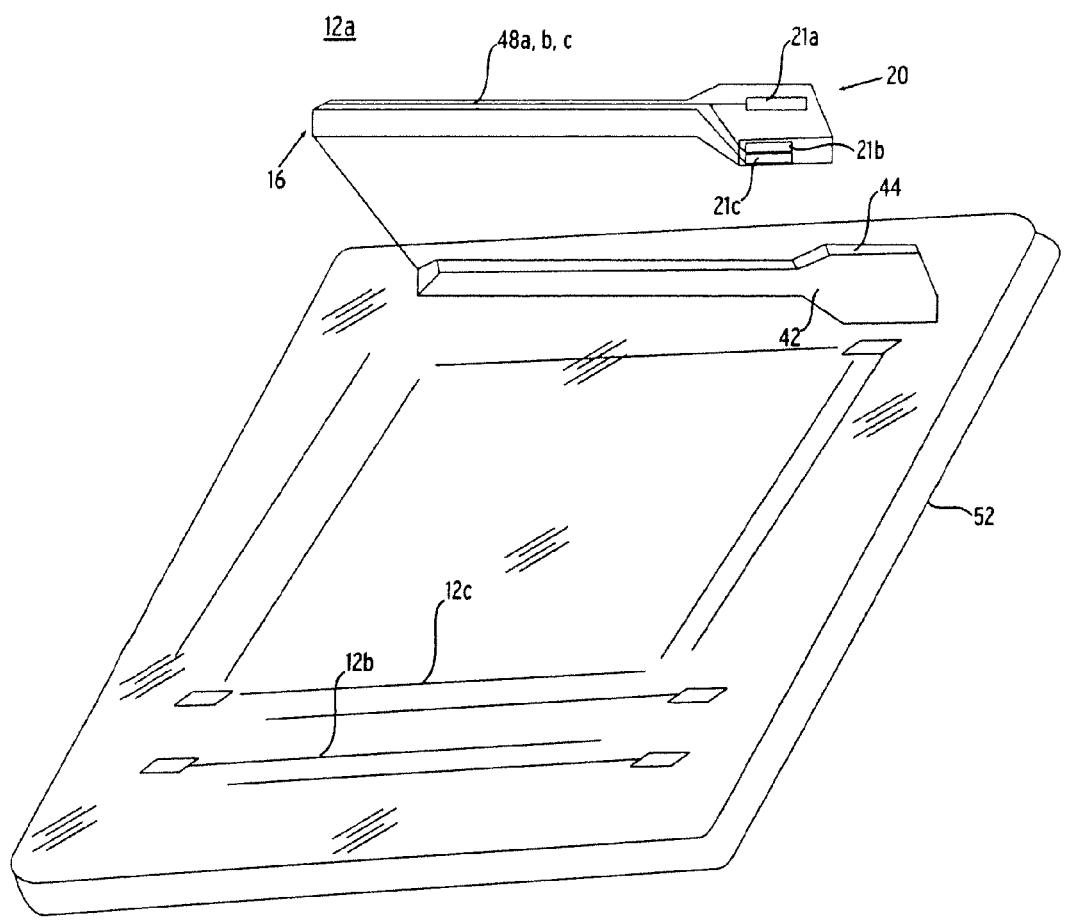
FIG. 7 is an exploded perspective view illustrating a plurality of thin film electrochemical sensors formed on a rigid flat substrate according to an embodiment of the invention.

One or more sensors are formed on a rigid flat substrate, such as a glass plate or a ceramic. When finished, the sensors may be removed from the rigid flat substrate by a suitable method, such as laser cutting. Other materials that can be used for the substrate include, but are not limited to, stainless steel, aluminum, and plastic materials. As seen in FIG. 7, the flexible sensors 12a, 12b, and 12c are formed in a manner which is compatible with photolithographic mask and etch techniques, but where the sensors 12a, 12b, and 12c are not physically adhered or attached directly to the substrate 52. Each sensor comprises a plurality of thin film electrodes 18a, 18b, and 18c formed between an underlying insulative base layer 42 and an insulative cover layer 44. A plurality of elongated conductive traces 48a, 48b, and 48c may connect the proximal segment end 20 to the distal segment end 16. At the proximal segment end 20, contact pads 21a, 21b, and 21c are formed. Apertures (not shown) formed in the insulative cover layer expose the distal end 16 portion of the electrodes 18a, 18b, and 18c so that they are in direct contact with patient blood or extracellular fluid.

Figure 5:
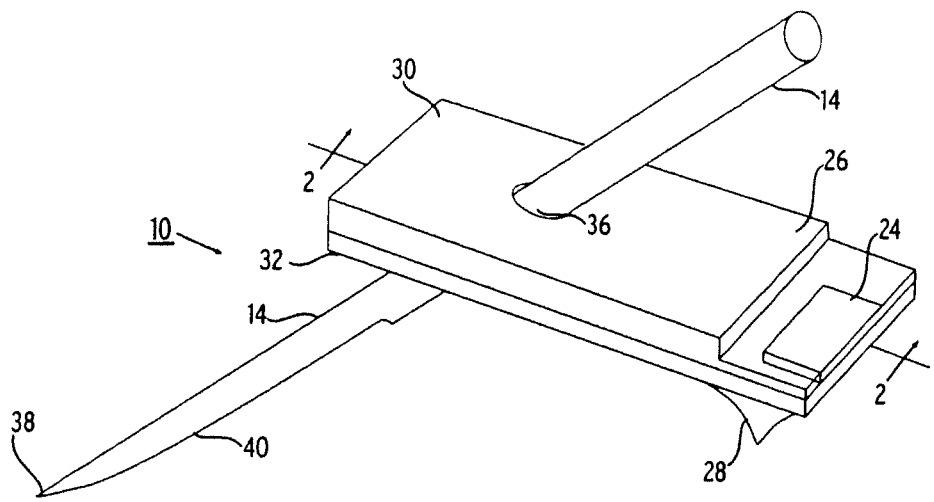
FIG. 5 is a perspective view illustrating a transcutaneous sensor insertion set according to an embodiment of the invention.
Figure 6:
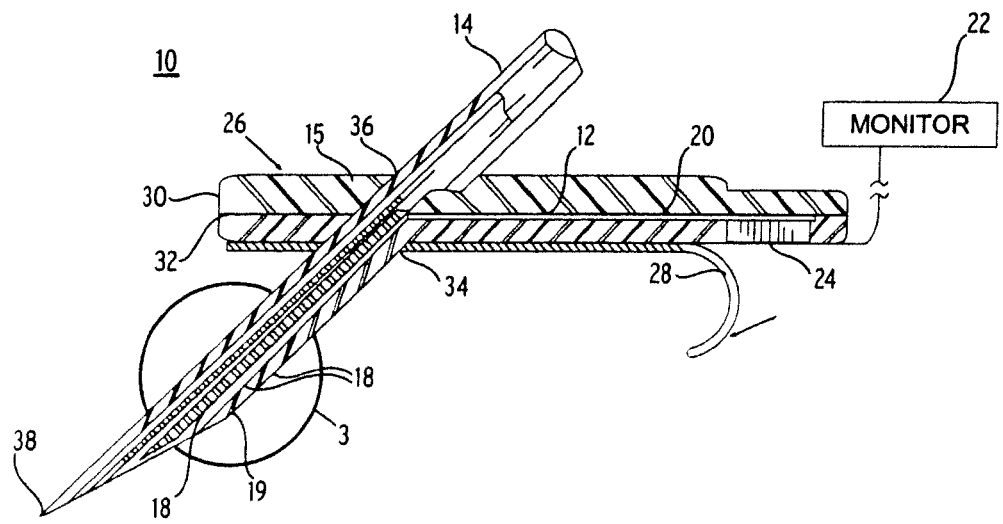
FIG. 6 is an enlarged longitudinal vertical section taken generally on the line 2-2 of FIG. 5 according to an embodiment of the invention.

In one embodiment of a sensor set, shown in FIGS. 5 and 6, a flexible electrochemical sensor 12 is constructed according to so-called thin film mask techniques to include elongated thin film conductors embedded or encased between layers of a selected insulative material such as polyimide film or sheet. The sensor electrodes 18 (shown in exaggerated form in the drawings) at a tip end of the sensor distal segment 16 are exposed through one of the insulative layers for direct contact with patient fluids, such as blood and/or interstitial fluids, when the sensor is transcutaneously placed. FIG. 6 shows how the distal segment 16 is joined to a proximal segment 20, the end of which terminates in suitable conductive contact pads or the like which are also exposed through one of the insulative layers. As illustrated schematically in FIG. 6, the proximal segment 20 and the contact pads thereon are adapted for electrical connection to a suitable monitor 22 for monitoring patient condition in response to signals derived from the sensor electrodes 18. The sensor electronics may be separated from the sensor by wire or be attached directly on the sensor. For example, the sensor may be housed in a sensor device including a housing that contains all of the sensor electronics, including any transmitter necessary to transmit data to a monitor or other device. The sensor device alternatively may include two portions, one portion housing the sensor and the other portion housing the sensor electronics. The sensor electronics portion could attach to the sensor portion in a side-to-side or top-to-bottom configuration, or any other configuration that would connect the two portions together. If the sensor electronics are in a housing separated by a wire from the sensor, the sensor electronics housing may be adapted to be placed onto the user's skin or placed on the user's clothing in a convenient manner. The connection to the monitor 22 may be wired or wireless. In a wired connection, the sensor electronics may essentially be included in the monitor instead of in a housing with the sensor. Alternatively, sensor electronics may be included with the sensor as described above. A wire could connect the sensor electronics to the monitor. Examples of wireless connection include, but are not limited to, radio frequency, infrared, WiFi, ZigBee and Bluetooth. Additional wireless connections further include single frequency communication, spread spectrum communication, adaptive frequency selection and frequency hopping communication. In further embodiments, some of the electronics may be housed on the sensor and other portions may be in a detachable device. For example, the electronics that process and digitize the sensor signal may be with the sensor, while data storage, telemetry electronics, and any transmission antenna may be housed separately. Other distributions of electronics are also possible, and it is further possible to have duplicates of electronics in each portion. Additionally, a battery may be in one or both portion. In further embodiments, the sensor electronics may include a minimal antenna to allow transmission of sensor data over a short distance to a separately located transmitter, which would transmit the data over greater distances. For example, the antenna could have a range of up to 6 inches, while the transmitter sends the information to the display, which could be over 10 feet away.

Further description of flexible thin film sensors of this general type may be found in U.S. Pat. No. 5,482,473, which is incorporated by reference herein. The proximal segment 20 may be conveniently connected electrically to the monitor 22 by means of a connector block 24 as shown and described in U.S. Pat. No. 5,482,473, which is also incorporated by reference herein.

The overall sensor height of the sensor 12 (from base to top insulative layer) may be about 0.001 inches or 25 microns. The base layer is about 12 microns and each insulative layer is about 5 microns. The conductive/electrode layers are each in the range of several thousand angstroms. Any of these layers could be thicker if desired. The overall width of the sensor is as small as about 150 microns. It could be slightly larger, about 250 microns or 0.010 inches. The width could also larger if desired. The length of the sensor is dependant on how deep the tissue is at the placement site. For example, for subcutaneous sensing, the sensor length may be about 0.50 inches to about 1.5 inches, for example, about 1 inch.

The sensor 12 is carried by a mounting base 26 adapted for placement onto the skin of a patient. As shown, the mounting base 26 comprises an enlarged and generally rectangular pad having an underside surface coated with a suitable pressure sensitive adhesive layer, with a peel-off paper strip 28 normally provided to cover and protect the adhesive layer, until the insertion set 10 is ready for use. As shown in FIGS. 5 and 6, the mounting base comprises upper and lower layers 30 and 32, with the proximal segment 20 of the flexible sensor 12 sandwiched between. The proximal sensor segment 20 has a forwardmost end joined to the distal segment 16 which is folded angularly to extend downwardly through a slot 34 formed in the lower base layer 32.

The insertion needle 14 is adapted for slide-fit reception through a needle port 36 formed in the upper base layer 30 and further through the lower slot 34 in the lower base layer 32. As shown in FIG. 5, the insertion needle 14 has a sharpened tip 38 and an open slot 40 which extends longitudinally from the tip 38 at the underside of the needle to a position at least within the slot 34 in the lower base layer 32. Above the mounting base 26, the insertion needle 14 may have a full round cross sectional shape and is desirably closed at a rear end. In the preferred embodiment, the slotted needle 14 has a part-circular cross sectional shape, with an arcuate dimension or span greater than 180 degrees, such as on arcuate dimension of about 210 degrees. This leaves a longitudinal slot in the needle with an arcuate dimension of about 150 degrees.

The cannula 15 is shown in FIG. 6 and comprises a part circular cross section fitted within the insertion needle 14 to extend downwardly from the mounting base 26. This cannula 15 is constructed from a suitable medical grade plastic or elastomer, such as polytetrafluoroethylene, silicone, or the like. The cannula 15 has one end fitted into the slot 34 formed in the lower layer 32 of the mounting base 26, wherein the cannula 15 is desirably secured to the mounting base by a suitable adhesive or other selected attachment means. From the mounting base 26, the cannula extends angularly downwardly with its first portion nested within the insertion needle 14, terminating slightly before the needle tip 38. One or more apertures 19 are formed in the cannula 15 near the distal segment end 16, in general alignment with the sensor electrodes 18, to permit direct electrode exposure to patient body fluid when the sensor is transcutaneously placed.

In use, the insertion set 10 permits quick and easy transcutaneous placement of the sensor distal segment 16 at a selected site within the body of the patient. More specifically, the peel-off strip 28 is removed from the mounting base 26, at which time the mounting base 26 can be pressed onto and seated upon the patient's skin. During this step, the insertion needle 14 pierces the patient's skin and carries the protective cannula 15 with the sensor distal segment 16 therein to the appropriate transcutaneous placement site. During insertion, the cannula 15 provides a stable support and guide structure to carry the flexible sensor to the desired insertion site.

When the sensor 12 is transcutaneously placed, with the mounting base 26 seated upon the patient's skin, the insertion needle 14 can be slidably withdrawn from the patient. The slotted needle geometry permits the insertion needle 14 to slide over and longitudinally separate from the second portion of the cannula 15, thereby leaving the cannula 15 as well as the sensor distal segment 16 with electrodes 18 at the selected insertion site. These electrodes 18 are directly exposed to patient body fluid via the apertures 19. The sensor proximal segment 20 is appropriately coupled to the monitor 22, so that the sensor 12 can then be used over a prolonged period of time for taking blood chemistry readings, such as BG readings in a diabetic patient. In an embodiment, when the insertion needle is withdrawn, a protective sheath (not shown) contained in the mounting base is dislodged and covers the needle tip as the needle is separated from the mounting base. If desired, the cannula 15 can also be used to deliver medication and/or sensor calibration fluid to the vicinity of the electrodes 18, or alternately to withdraw patient fluid such as blood for analysis.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

EXAMPLES

The examples set forth below are illustrative of different compositions and conditions that can be used in practicing the invention. All proportions are by weight unless otherwise indicated. It will be apparent, however, that the invention can be practiced with many types of compositions and can have many different uses in accordance with the disclosure above and as pointed out hereinafter.

Example I

Step 1: Counter Electrode Metallization Step

A KAPTON® polyimide base is used as a base layer and spin coated on a rigid substrate, such as glass. The first metallization comprised sputter-based chrome, gold and top-chrome. The top chrome pattern was photoresisted using photomask to protect the metallized trace and counter electrode. The uncovered areas of the base-chrome and gold were etched. The etching was performed at 50° C. for the gold and at ambient temperature for the chrome. The strip photoresisting was performed in isopropyl alcohol ("IPA") at ambient temperature, and then again on all areas except the counter electrode, bond pad, and plating pad, at ambient temperature. A second etching was then performed on the top-chrome of all uncovered areas at ambient temperature. Strip photoresisting was performed again in IPA at ambient temperature. Polyimide was spin coated on as an insulative layer. Photo-imaging was then performed to cure specific areas. The resulting electrode layer was developed and rinsed.

Step 2: Working Electrode Metallization Step

The next electrode layer is formed generally above the counter electrode layer. This second metallization step involves the same sputter base-chrome and gold as a base layer. Photoresisting is performed using photomask to protect the working metallized trace and working electrode being formed. Etch is performed on the uncovered areas at 50° C. for the gold and at ambient temperature for the chrome. Strip photoresisting is again performed in WA at ambient temperature. Next, photoresisting is performed on all areas except the counter electrode, bond pad, and plating pad. Etching is performed on all uncovered areas of the top-chrome at ambient temperature. Strip photoresisting is performed in IPA at ambient temperature. Polyimide was spin coated on as an insulative layer. Photoimaging was then performed to cure specific areas. The resulting electrode layer was developed and rinsed.

Step 3: Reference Electrode Metallization Step

The next electrode layer is formed generally above the counter electrode layer. This third metallization step also involves the sputter base-chrome and gold combination as a base layer. Photoresisting is performed using photomask to protect the working metallized trace and working electrode being formed. Etch is performed on the uncovered areas at 50° C. for the gold and at ambient temperature for the chrome. Strip photoresisting is again performed in WA at ambient temperature. Next, photoresisting is performed on all areas except the counter electrode, bond pad, and plating pad. Etching is performed on all uncovered areas of the top-chrome at ambient temperature. Strip photoresisting is performed in IPA at ambient temperature. Polyimide was spin coated on as an insulative layer. Photoimaging was then performed to cure specific areas. The resulting electrode layer was developed and rinsed. After all three electrode layers are formed, the layers are subjected to a final bake at a high temperature, such as 325° C.

What is claimed is:

1. A method of making a flexible analyte sensor, the method comprising:
   providing a base layer;
   forming a first electrode layer on the base layer, wherein the first electrode layer includes a first electrode;
   forming a first insulative layer on the first electrode layer, said first insulative layer having opposed first and second longitudinal ends;
   forming a first aperture in the first insulative layer to expose at least a portion of the first electrode, said first aperture being disposed longitudinally between, and away from, said first and second longitudinal ends of the first insulative layer;
   forming a second electrode layer on the first insulative layer, wherein the second electrode layer includes a second electrode;
   forming a second insulative layer on the second electrode layer, said second insulative layer having opposed first and second longitudinal ends; and
   forming a second aperture in the second insulative layer to expose at least a portion of the second electrode, said second aperture being disposed longitudinally between, and away from, said first and second longitudinal ends of the second insulative layer,
   wherein the first and second electrodes are in a staggered configuration.

2. The method of claim 1, wherein the maximum height of the sensor is about 25 microns.

3. The method of claim 1, wherein the providing a base layer includes spin coating polyimide onto a rigid substrate.

4. The method of claim 1, wherein the forming a first electrode layer includes surface sputtering a chrome-based layer on the base layer.

5. The method of claim 4, wherein the forming a first electrode layer further includes surface sputtering a gold-based layer on the chrome-based layer.

6. The method of claim 1, wherein the forming a first insulative layer includes spin-coating polyimide onto the second electrode layer.

7. The method of claim 1, wherein the first and second apertures are formed by a photoresist process.

8. The method of claim 1, further comprising depositing platinum black on one or more of the first and second electrodes.

9. The method of claim 1, further comprising:
   forming a third electrode layer on the second insulative layer, wherein the third electrode layer includes a third electrode;
   forming a third insulative layer above the third electrode layer, said third insulative layer having opposed first and second longitudinal ends; and
   forming a third aperture in the third insulative layer to expose at least a portion of the third electrode, said third aperture being disposed longitudinally between, and away from, said first and second longitudinal ends of the third insulative layer.

10. The method of claim 9, further comprising depositing one or more compounds selected from the group consisting of silver and silver chloride on the third electrode.

11. The method of claim 10, further comprising coating at least a portion of the first electrode and the second electrode with an enzyme layer including glucose oxidase.

12. The method of claim 11, further comprising vapor cross-linking the enzyme layer.

13. The method of claim 11, wherein the enzyme layer further includes albumin.

14. The method of claim 11, further comprising forming an adhesion promoter layer above the enzyme layer.

15. The method of claim 11, further comprising forming a glucose limiting membrane over the enzyme layer.

16. The method of claim 15, wherein the glucose limiting membrane comprises at least one of a silane and polyamine.

17. The method of claim 15, further comprising forming a hydrophilic layer over the glucose limiting membrane.

18. The method of claim 9, wherein the first, second, and third electrodes are in a staggered configuration.

19. The method of claim 18, wherein the third electrode layer is disposed directly above the second electrode layer, and the second electrode layer is disposed directly above the first electrode layer.

20. The method of claim 9, wherein one of the electrodes is a counter electrode, one of the electrodes is a reference electrode, and one of the electrodes is a working electrode.

21. The method of claim 9, wherein the first insulative layer is disposed directly on the first electrode layer without any intervening layers.

22. The method of claim 9, wherein the second electrode layer is disposed directly on the first insulative layer without any intervening layers.

23. The method of claim 9, wherein the second insulative layer is disposed directly on the second electrode layer without any intervening layers.

24. The method of claim 9, wherein the third electrode layer is disposed directly on the second insulative layer without any intervening layers.

25. The method of claim 9, wherein the third insulative layer is disposed directly on the third electrode layer without any intervening layers.

26. The method of claim 9, wherein the forming the first electrode layer further includes forming a first conductive trace leading from the first electrode to a first conductive pad configured to electrically connect to sensor electronics, the forming the second electrode layer further includes forming a second conductive trace leading from the second electrode to a second conductive pad configured to electrically connect to sensor electronics, and the forming the third electrode layer further includes forming a third conductive trace leading from the third electrode to a third conductive pad configured to electrically connect to sensor electronics.

27. The method of claim 26, wherein the sensor electronics communicate wirelessly with a monitor.

* * * * *